(12) United States Patent
Shershukov et al.

(10) Patent No.: US 6,713,636 B2
(45) Date of Patent: Mar. 30, 2004

(54) THIOXANTHONE DYES WITH IMPROVED SOLUBILITY AND A METHOD OF PREPARING 2-OXYBENZANTHRONES AS INTERMEDIATE MATERIALS FOR MAKING OF THESE DYES

(75) Inventors: Viktor Mihailovich Shershukov, Kharkiv (UA); Alexander Nikolayevich Artukhov, Kupryansk-Uzlovoy (UA)

(73) Assignee: 3M Innovative Properties Company, St. Paul, MN (US)

( * ) Notice: Subject to any disclaimer, the term of this patent is extended or adjusted under 35 U.S.C. 154(b) by 82 days.

(21) Appl. No.: 10/207,435

(22) Filed: Jul. 29, 2002

(65) Prior Publication Data

US 2003/0061671 A1 Apr. 3, 2003

(30) Foreign Application Priority Data

Aug. 20, 2001 (UA) ........................ 2001085839

(51) Int. Cl.⁷ ........................... C07D 495/22
(52) U.S. Cl. ........................................ 549/24
(58) Field of Search ............................. 549/24

(56) References Cited

U.S. PATENT DOCUMENTS

| 3,356,687 A | 12/1967 | Fuchs et al. |
| 3,785,989 A | 1/1974 | Noetzel et al. |
| 3,828,072 A | 8/1974 | Spietschka et al. |
| 3,829,439 A | 8/1974 | Spietschka et al. |
| 4,036,859 A | 7/1977 | Ribaldone et al. |
| 4,116,923 A | 9/1978 | Gattner et al. |
| 4,740,604 A | 4/1988 | Weis et al. |
| 5,280,128 A | 1/1994 | Ribaldone et al. |
| 5,415,669 A | 5/1995 | Buhler et al. |
| 6,110,566 A | 8/2000 | White et al. |
| 6,531,613 B1 * | 3/2003 | Olson ........................ 549/41 |

FOREIGN PATENT DOCUMENTS

| DE | DE-A2815031 | 10/1979 |
| FR | 2315496 | 1/1977 |
| IT | 1061813 | 4/1983 |
| JP | 10308278 | 11/1998 |
| JP | 10312885 | 11/1998 |
| WO | WO 90/01526 | 2/1990 |

OTHER PUBLICATIONS

Moore, J.A. (ed.), *Macromolecular Syntheses*, 1977, vol. 1, pp. 17–21.

Carlini et al., Dyes and Pigments, *New Daylight Fluorescent Pigments*, 1982, vol. 3, pp. 59–69.

* cited by examiner

*Primary Examiner*—Joseph K. McKane
*Assistant Examiner*—Kamal Saeed
(74) *Attorney, Agent, or Firm*—Carolyn A. Fischer

(57) ABSTRACT

The invention relates to new thioxanthone compounds having utility as fluorescent dyes and processes for their manufacture.

5 Claims, No Drawings

THIOXANTHONE DYES WITH IMPROVED SOLUBILITY AND A METHOD OF PREPARING 2-OXYBENZANTHRONES AS INTERMEDIATE MATERIALS FOR MAKING OF THESE DYES

RELATED APPLICATIONS

This application claims foreign priority to Ukraine patent application no. 2001085839 filed Aug. 20, 2001.

FIELD OF THE INVENTION

The invention relates to new thioxanthone compounds having utility as fluorescent dyes and processes for their manufacture.

BACKGROUND OF THE INVENTION

Benzothioxanthone compounds are known as fluorescent colorants.

Dyes described in U.S. Pat. Nos. 3,828,072 and 5,280,128 have the common formula:

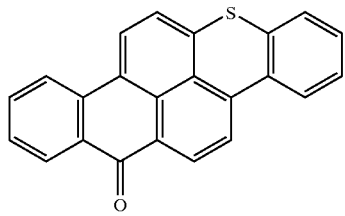

However, these compounds are luminescent in the orange-red region and difficult to synthesize while using undesirable components.

In particular, 14H-anthra[2,1,9-mna]thioxanthene-14-one thioxanthone colorants have been described by Carlini et al. in *Dyes and Pigments,* Vol. 3 (1982), pps. 59–69. One such colorant described by Carlini is 6-methoxy-14H-anthra[2,1,9-mna]thio xanthene-14-one. It is a photostable fluorescent colorant in the red region ($\lambda_{max}$=614 nM). However, this colorant has the disadvantage of being poorly soluble in organic solvents and polymer materials.

The known compounds can be prepared using the schematic diagram:

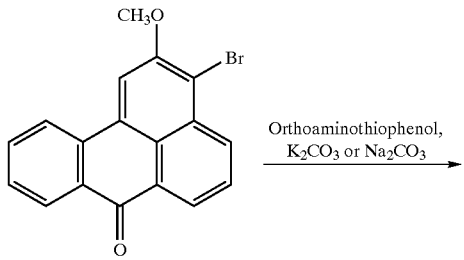

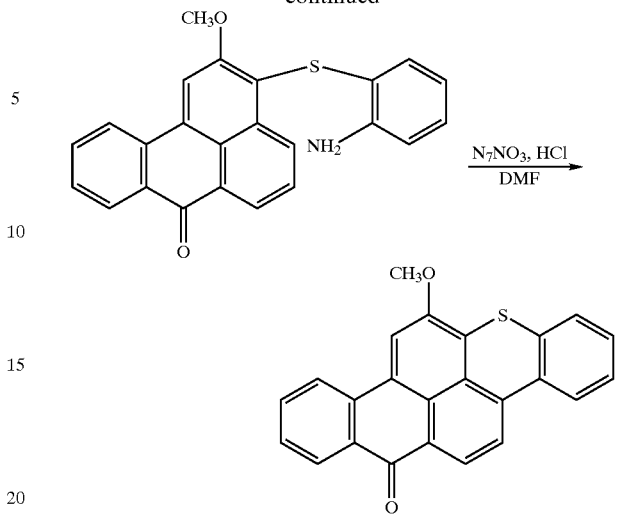

A method for preparing intermediates for synthesis is described in U.S. Pat. No. 4,036,859, IPC C09B, 3/02, 3/04, 1977. The method is based on the schematic diagram:

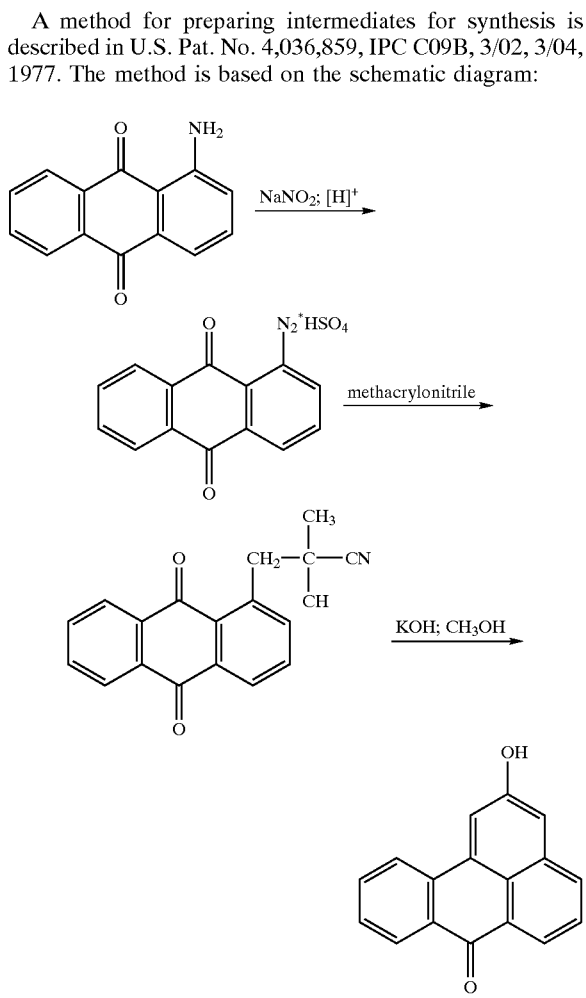

and includes the following stages:
(a) reacting of 1-aminoanthroquinone with sodium nitrite in sulfuric acid to form sulfate salt of anthroquinoyl diazonium;
(b) treatment of the diazonium salt by metakrylonitril in presence of a catalytic amount of cuprous halide in methyl alcohol to form compounds 3-(1-anthro quinoyl)-2-hydroxi-2-methylpropionitril (c) reacting of the formed compound with potassium hydroxiyl in methyl alcohol to form a red reaction mass. This mass is then filtered of contaminants, poured on acidified water and 2-oxibenzathron is extracted. It has yellow color and melt temperature of 297–298° C., yield—81%.

A drawback of this method for making the intermediate 2-oxybenzanthrone product is utilization of methanol.

SUMMARY OF THE INVENTION

The invention relates to new chemical components of the thioxanthone series of the type 14H-anthra[2,1,9-mna]thioxanthene-14-one, in particular, 6-n-octyloxy-14H-anthra[2,1,9-mna]thioxanthene-14-one of the general formula

I

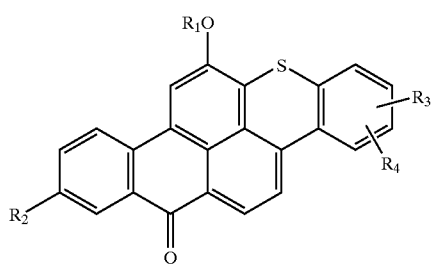

wherein $R_1$ is a straight chain alkyl group having from 6 to 22 carbon;

$R_2$, $R_3$ and $R_4$ are each, independently, hydrogen or alkyl having from 1 to 4 carbon atoms, and, in particular, 6-n-octyloxy-14H-anthra(2,1,9-mna)thioxanthene-14-one.

These compounds have utility as fluorescent dyes and exhibit significant luminescence in the red spectral region ($\lambda_{max}$=615 nM).

The compounds are well soluble in organic solvents and exhibit intense luminescence in solvents with various polarity.

These properties of claimed compounds allow their efficient utilization as an active media for liquid lasers, day light fluorescent dyes and in other industries.

The second aspect of the present invention includes an improved process for preparing key intermediates in the manufacture of compounds of formula I. These improved methods include a process for preparing a compound of the formula (II):

II

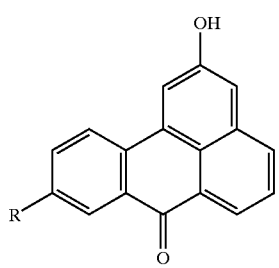

wherein R is hydrogen or alkyl having from 1 to 4 carbon atoms.

DETAILED DESCRIPTION OF THE PREFERRED EMBODIMENTS

A purpose of the invention is to develop new chemical colorants in the benzothioxanthone series with red fluorescence and improved solubility in organic solvents, a longer spectrum in the red region and higher light stability. The second goal is a better method of making the 2-oxybenzanthrone product that will increase yield of transitional and final products under more favorable manufacturing conditions.

This problem is solved by development of new benzothioxanthone colorants with the generic formula I:

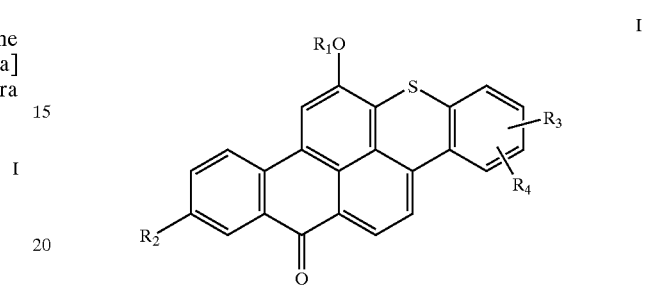

wherein $R_1$ is a straight chain alkyl group having from 6 to 22 carbon;

$R_2$, $R_3$ and $R_4$ are each, independently, hydrogen or alkyl having from 1 to 4 carbon atoms.

The compounds have improved solubility.

Particularly useful compounds described above include those where $R_2$, $R_3$ and $R_4$ of the formula I are hydrogen, particularly valuable compounds where $R_1$ is a straight chain octyl group. A particularly valuable dye of the present invention is 6-n-octyloxy-14H-anthra(2,1,9-mna)thioxanthene-14-one.

The compounds of formula I may be prepared by known methods or by the improved process of the invention.

By way of illustration, the following schematic diagram shows a method of making of one of the claimed components the 6-n-octyloxy-14H-anthra(2,1,9-mna)thioxanthene-14-one.

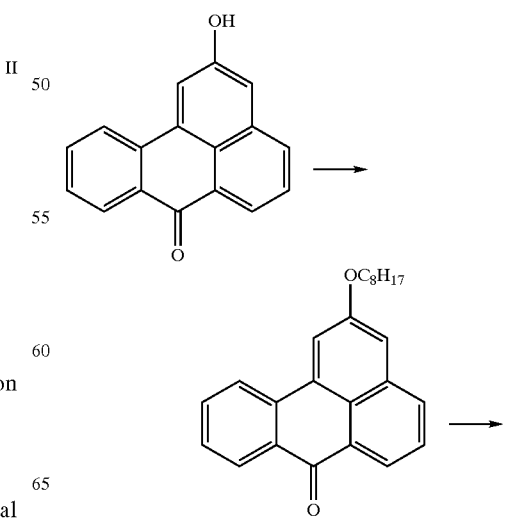

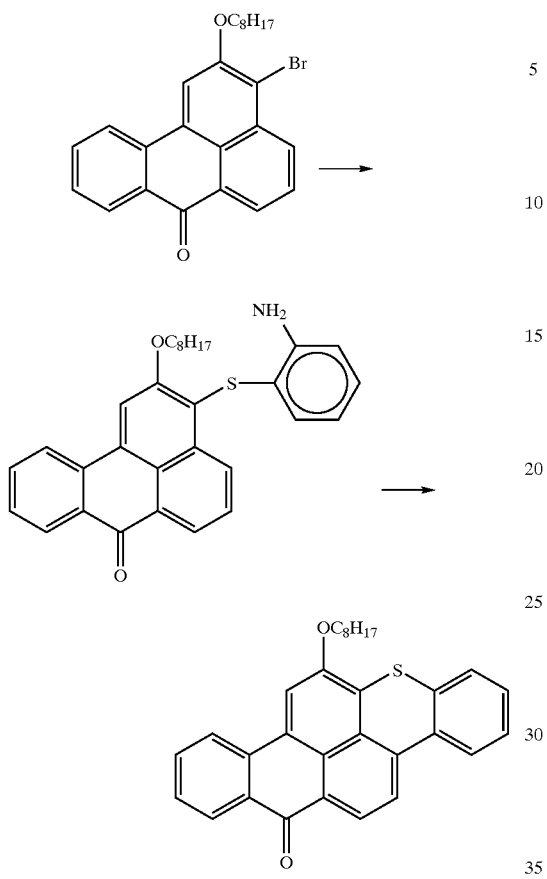

Generally, a 2-oxybenzanthrone may be alkylated with an alkyl halide in the presence of sodium or potassium carbonate in a polar-aprotic solvent to provide the desired 2-alkoxy compound. Bromination of the alkoxy compound with n-bromo succinimide in the presence of glacial acetic acid provides the neighboring 3-bromo substituent, which is then reacted with ortho-amino thiophenol at reflux in a polar-aprotic solvent such as, for example, dimethylformamide (DMF). The product is then ring-closed by treatment with hydrochloric acid, followed by reaction with sodium nitrite and then addition of a copper sulfate catalyst.

The above-described synthesis of the compounds of the present invention employs 2-oxybenzanthrones as intermediate materials.

The present invention also includes the process for manufacturing 2-oxybenzanthrones of the formula (II):

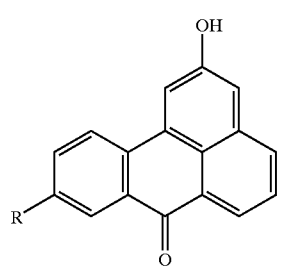

wherein R is hydrogen or alkyl having from 1 to 4 carbon atoms, comprising:

(a) reacting a compound of the formula III

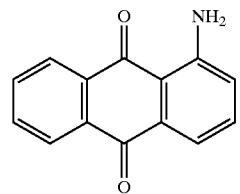

with an alkali metal nitrite in the presence of an acid to form a diazonium acid salt;

(b) reacting the diazonium salt with isopropenyl acetate and a catalytic amount of a cuprous halide (I) in a solvent to form a compound of the formula (IV):

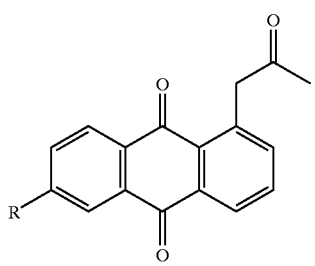

and (c) reacting the compound of the formula of step (b) with a base in an alcohol solvent at the reflux temperature of the solvent; subsequently adding a sufficient amount of acid to render the pH between about 4 and 5 and collecting the desired compound.

According to the invention, the reaction described in step (b) of the diazonium salt with isopropenyl acetate and a catalytic amount of a cuprous halide is conducted in a mixture of acetonitrile and water in 1:1 ratio.

In particular, the improvement is achieved in the synthesis of the compound with formula (V)

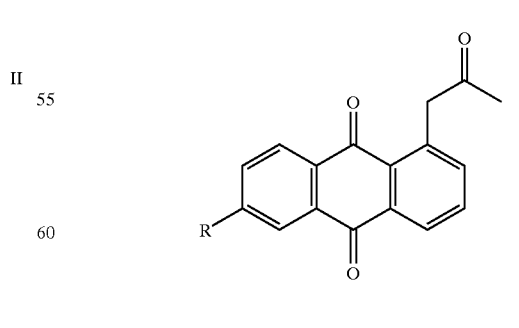

wherein R is hydrogen or alkyl having 1 to 4 carbon atoms and including the reaction of the formula (VI):

VI

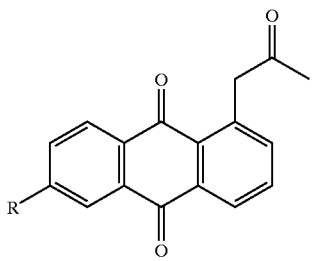

wherein X is a residue of sulfuric or hydrochloric acid with isopropenyl acetate and a catalytic amount of cuprous halide in a mixture of acetonitrile and water solution in a 1:1 volume ratio.

In step (a), the preferred acid is concentrated sulfuric acid which forms the diazonium sulfate salt; however hydrochloric or hydrobromic acid may be used, resulting in the formation of a diazonium halide salt. In step (c), the preferred base is an alkali metal hydroxide, for example, sodium or potassium hydroxide.

The compounds of the present invention are useful as red color fluorescent dyes.

Objects and advantages of the invention are further illustrated by the following examples, but the particular materials and amounts thereof recited in the examples, as well as other conditions and details, should not be construed to unduly limit the invention. All parts, percentages and ratios herein are by weight unless otherwise specified.

SPECIFIC EXAMPLES

Example 1

6-n-Octyloxy-14H-anthra(2,1,9 mna)thioxanthene-14-one

A. Preparation of Sulfate Salt of Anthroquinoyl Diazonium.

Into a three necked 0.5 liter round bottom flask, containing 150 ml of concentrated sulfuric acid and equipped with a thermometer and a mechanical stirrer, and immersed into an ice bath, 17 g (0.246 M) of finely ground sodium nitrite powder was added in portions, carefully maintaining the reaction temperature below 10° C. Upon the completion of the sodium nitrite addition, the ice bath was removed and the introduction of 50 g (0.224 M) of 1-aminoanthroquinone commenced. A slow rise in temperature was observed. Upon the completion of the 1-aminoanthraquinone addition (here the reaction mass color changed from yellow-green to reddish-brown), the reaction mixture was heated to 50° C. and held at 50° C. for 20 minutes, and then allowed to cool to room temperature.

The cooled reaction mixture was decanted after mixing in a beaker into which 350 g of finely chopped ice had been placed. After the light green mass of the diazonium sulfate salt heated the ice to melting, it was filtered and washed with water (50 ml) and acetone (30 ml); $T_m$=158–165° C. The diazonium sulfate salt was used as such in the next step.

B. Preparation of 1-acetonylanthraquinone.

Diazonium sulfate salt from Step A (74.4 g; based on assumed theoretical yield) was placed into a three-neck flask, equipped with a mechanical stirrer and a thermometer, and to it was added 150 ml of water, 150 ml acetonitrile and 96 moles isopropenyl acetate. The mixture was heated to 35–40° C. while stirring, and copper monochloride (1.8 g) was added portion-wise as the catalyst. Evolving bubbles of gaseous nitrogen, accompanied by an increase in temperature were observed. After the addition of the final portion of the copper monochloride during which no nitrogen was evolved, the temperature of the reaction mixture was raised to 60° C. and held at that temperature for 30 minutes. At this point the intermediate product of the reaction surfaced and floated as an amorphous substance, and subsequently settled in a powder-like form. To the reaction mass, cooled to room temperature was added 100 ml of water. The precipitate was filtered and washed until the rinsing water remained at neutral pH. The product thus obtained was lightly gray in color; $T_m$=170–175° C. The 1-acetonylanthraquinone was used as such in the next step.

C. Preparation of 2-hydroxy-7H-benzo[de]anthracene-7-one.

1-Acetonylanthraquinone from Step B (59 g; based on assumed theoretical yield) was placed into a 1 liter round bottom flask, 500 ml of EtOH and 25 g KOH were added. This mixture was refluxed for one hour. As the solution heated up, it turned dark red. After the one-hour reflux, the mixture was filtered and decanted into a 2-liter beaker. Water (500 ml) was added and to this, a sufficient amount of 35% HCl to render the pH value between 4 and 5. Immediately a bright red precipitate, 2-hydroxy-7H-benzo[de] anthracene-7-one, fell out of solution. It was filtered and washed with water; $T_m$=275–280° C.; yield (based on 1-aminoanthra-quinone)=50 g (91%).

D. Preparation of 2-n-octyloxy-7H-benzo[de]anthracene-7-one.

2-Hydroxy-7H-benzo[de]anthracene-7-one (50 g; 0.203M), 30.8 g potassium carbonate (0.223M); heated for 3 hours at 250° C. to remove water), 55 ml of n-octyl bromide and 150 ml DMF were placed into a 0.5 liter two-necked round bottom flask equipped with a mechanical stirrer and a thermometer. The mixture was heated to 100° C. for 5 hours under stirring and then allowed to cool to room temperature. The precipitate was filtered and washed with water, ethanol (50 ml) and hexane (50 ml). The product had a light greenish color; $T_m$=94–98° C.; yield=69 g (95%).

E. Preparation of 2-n-octyloxy-3-bromo-7H-benzo[de] anthracene-7-one.

2-n-Octyloxy-7H-benzo[de]anthracene-7-one (71.6 g; 0.2 M) was placed into a 0.5 liter round bottom flask equipped with a mechanical stirrer. N-bromo-succinimide (40.0 g; 0.24M) and 350 ml of glacial acetic acid were added. The bromination took place in a water bath at 60° C. for three hours under stirring. The reaction was cooled and filtered. The precipitate was washed with glacial acetic acid (50 ml) and then with hot water (300 ml). The yellow color product had a $T_m$=95–103° C.; yield=79.5 g (91%).

F. Preparation of 3-[(2-aminophenyl)thio]-2-n-octyloxy-7H-benzo[de]anthracene-7-one.

Into a 0.5 liter single necked round bottom flask, containing 78.7 g of 2-n-octyloxy-3-bromo-7H-benzo[de] anthracene-7-one (0.18M), was added 21 g (0.2M) of 90% ortho-aminothiophenol, 23.8 g (0.22M) sodium carbonate and 300 ml of DMF. The reaction was boiled for two hours or until thin layer chromatography using chloroform as the elutant indicated the disappearance of the bromo-derivative. The mixture was cooled and 150 ml of water was added. The mixture was stirred and the light brown precipitate was filtered. The precipitate was washed until it stopped coloring the wash waters. The yield=79.7 g (92%); $T_m$=118–124° C.

G. Preparation of 6-n-octyloxy-14H-anthra(2,1,9-mna) thioxanthene-14-one.

Into a 2 liter three-necked round bottom flask, equipped with a mechanical stirrer and a thermometer, containing 77 g 3-[(2-aminophenyl)thio]-2-n-octyloxy-7H-benzo[de]

anthracene-7-one (0.16M), placed into an ice bath, was added 1100 ml of DMF. The mixture was cooled to 10° C. while stirring. 35% Hydrochloric acid (247 ml) was added portionwise, ensuring that the reaction temperature did not exceed 20° C. After the HCl addition was complete, the reaction was cooled to 0° C. and a solution of 14.0 g (0.2M) NaNO$_2$ in 78 ml of H$_2$O was added portionwise, making sure that the reaction temperature did not rise above 5° C. The reaction mixture was held at 5° C. for an additional 1 hour after the completion of the sodium nitrite addition. Then, during the addition of 5.2 g copper sulfate catalyst, the reaction was heated, and at 15° C., nitrogen bubbles began to evolve. The reaction mass was held at 100° C. for 1.5 hours, cooled and the red colored precipitate was filtered and washed with water, then ethanol. The yield=66.89 g (90%); T$_m$=205–208° C.

Example 2

6-n-Octyloxy-11-methyl-14H-anthra(2,1,9 mna) thioxanthene-14-one

All reaction stages were performed similarly to Example 1 until the stage F.
F. Preparation of 3-[(2-amino-3-methylphenyl)thio]-2-n-octyloxy-7H-benzo[de]anthracene-7-one.
Into a single necked round bottom flask, containing 78.7 g of 2-n-octyloxy-3-bromo-7H-benzo[de]anthracene-7-one (0.18M), was added 34 g of 80% 2-methyl 6-mercapto aniline, 23.8 g (0.22M) sodium carbonate and 300 ml of DMF. The reaction was boiled until completion (based on a TCX check for absence of the original product). The mixture was cooled and 150 ml of water was added. The formed precipitate was washed until it stopped coloring the wash waters. The yield=79.2 g (89%); T$_m$=126–131° C.
G. Preparation of 6-n-octyl-11methyl-14H-anthra(2,1,9-mna)thioxanthene-14-one.
70 g (0.14M) of 3-[(2-amino-3-methylphenyl)thio]-2-octyloxy-7H-benzo[de]anthracene-7-one and 1200 ml of DMF were placed into a 2 liter three-necked flask, equipped with a mechanical stirrer and a thermometer. The flask was set onto an ice bath. While stirring, 235 mg of 36% of hydrochloric acid has been added at a temperature not exceeding 20° C. After the reaction mixture was cooled to 0° C., 13.1 g of a sodium nitrite solution in 70 ml of water was added portionwise and held for an hour. Then 0.5 g of copper sulfate (II) has been added at 10° C. and heated till 100° C. The mixture was held for 2 hours, cooled and filtered. The dark red colored precipitate was washed with ethanol and water. The yield=60 g (89. T$_m$=207–209° C.

Example 3

Solubility Comparison of the Claimed Compound and the Prototype

Two mixtures were prepared for comparison. The first one contained a dye prepared as per Example 1 by taking 0.1 g of the dye and adding chloroform until full solubility. The second mixture was prepared using 0.1 g of 6-methoxy-14H-anthra(2,1,9-mna)thioxanthene-14-one dye and also adding chloroform until its full solubility. At the end, 30 ml of chloroform was required to solute 0.1 g of the dye in the first mixture while 120 ml of the chloroform was required to solute the same amount of dye in case of the prototype. This fact indicates that the claimed dye has four-fold improvement in solubility in chloroform.

As it can be seen from the description and examples, the claimed structure has positive effect on spectral characteristics of the dyes, provides good solubility and light stability. An improvement in the method of making intermediates by means of substituting methanol as the solvent with a mixture of water-acetonitril increases yield from 81% to 92% and improves their purity. That significantly effects further preparation stages of the compound of the formula I, increases fluorescence intensity, introduces four-fold improvement in solubility and boosts yield of the final product till 90%. All that is achieved while maintaining high light stability and improved ecological manufacturing conditions.

We claim:
1. A compound of the thioxanthone series with improved solubility of the general formula

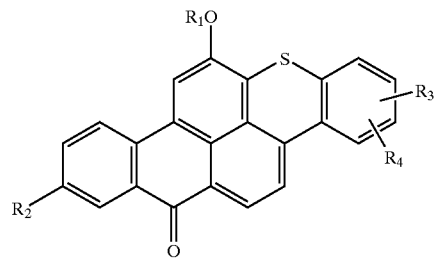

I wherein R$_1$ is a straight chain alkyl group having from 6 to 22 carbon atoms;

R$_2$, R$_3$ and R$_4$ are each, independently, hydrogen or alkyl having from 1 to 4 carbon atoms.

2. A compound of claim 1, wherein R$_1$ has 6 to 12 carbon atoms.

3. A compound of claim 1, wherein R$_2$, R$_3$ and R$_4$ are hydrogen.

4. A compound of claim 1, wherein R$_1$ is n-octyl.

5. A compound, being 6-(n-octyloxy)-14H-anthra(2,1,9-mna)thio-xanthene-14-one.

* * * * *

UNITED STATES PATENT AND TRADEMARK OFFICE
CERTIFICATE OF CORRECTION

PATENT NO. : 6,713,636 B2
DATED : March 30, 2004
INVENTOR(S) : Shershukov, Viktor M.

It is certified that error appears in the above-identified patent and that said Letters Patent is hereby corrected as shown below:

<u>Title page, Item [54] and Column 1, line 1,</u>
Title, delete "THLOXANTHONE" and insert -- THIOXANTHONE --, therefor.

<u>Column 8,</u>
Line 57, delete "chromatography" and insert -- chromotography --, therefor.

Signed and Sealed this

Eighth Day of March, 2005

JON W. DUDAS
*Director of the United States Patent and Trademark Office*